United States Patent
Swick (10) Patent No.: US 7,104,968 B2
(45) Date of Patent: Sep. 12, 2006

(54) APPLICATOR DEVICE FOR SUPPOSITORIES AND THE LIKE

(75) Inventor: Paul B. Swick, Lebanon, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 97 days.

(21) Appl. No.: 10/172,729

(22) Filed: Jun. 14, 2002

(65) Prior Publication Data

US 2003/0233077 A1 Dec. 18, 2003

(51) Int. Cl.
*A61M 31/00* (2006.01)
*A61M 5/00* (2006.01)
*A61M 5/315* (2006.01)
*A61K 9/02* (2006.01)

(52) U.S. Cl. ............... 604/57; 604/59; 604/60; 604/187; 604/218; 604/285; 604/288

(58) Field of Classification Search ........... 604/57–60, 604/73, 93.01, 104–109, 171–172, 181, 187, 604/218, 220, 264, 279, 285, 286, 288, 328–330, 604/11–16, 904

See application file for complete search history.

(56) References Cited

U.S. PATENT DOCUMENTS

| | | | | |
|---|---|---|---|---|
| 2,007,626 A | * | 7/1935 | Waring | 604/59 |
| 2,754,822 A | | 7/1956 | Emelock | |
| 3,297,031 A | * | 1/1967 | Bray | 604/59 |
| 3,424,158 A | | 1/1969 | Silver | |
| 3,667,465 A | * | 6/1972 | Voss | 604/59 |
| 3,884,233 A | | 5/1975 | Summey | |
| 3,934,584 A | * | 1/1976 | Corio | 604/59 |
| 4,341,211 A | | 7/1982 | Kline | |
| 4,361,150 A | | 11/1982 | Voss | |
| 4,421,504 A | | 12/1983 | Kline | |
| 4,496,341 A | | 1/1985 | Brucks | |

(Continued)

FOREIGN PATENT DOCUMENTS

| FR | 2610831 | 8/1988 |
|---|---|---|
| GB | 956679 | 4/1964 |
| GB | 2097259 | 11/1982 |

OTHER PUBLICATIONS

Pending U.S. Appl. No. 10/366,710 entitled "Applicator Device for Suppositories and the Like", filed Feb. 12, 2002, Inventor: Paul B. Swick.

*Primary Examiner*—Catherine S. Williams (57) ABSTRACT

An applicator for delivering pharmaceutical products or the like to a bodily cavity includes a barrel member having a distal end which is equipped with an opening. The applicator also includes a plurality of petals extending outwardly from the distal end and in a generally axial direction. The petals cooperate with the opening so as to form a receptacle for releasably receiving a pharmaceutical product in the distal end of the barrel member. Each of the petals has a truncated flexible tip sized and shaped so as to engage a substantially central portion of the pharmaceutical product such that a large section of the pharmaceutical product extends outwardly beyond the petals so as to facilitate the release of the pharmaceutical product from the receptacle. The device also includes a plunger member for releasing the pharmaceutical product from the receptacle. In accordance with the present invention, the device can be packaged in a package together with the pharmaceutical product received in the receptacle.

32 Claims, 8 Drawing Sheets

U.S. PATENT DOCUMENTS

| | | | |
|---|---|---|---|
| 4,536,178 A | | 8/1985 | Lichstein et al. |
| 4,543,086 A | * | 9/1985 | Johnson ........................ 604/11 |
| 4,563,182 A | * | 1/1986 | Stoy et al. .................... 604/285 |
| 4,588,395 A | | 5/1986 | Lemelson |
| 4,620,534 A | | 11/1986 | Zartman |
| 4,645,488 A | | 2/1987 | Matukas |
| 4,900,315 A | | 2/1990 | Lundqvist et al. |
| 4,990,136 A | | 2/1991 | Geria |
| D320,084 S | | 9/1991 | Stewart et al. |
| 5,087,239 A | | 2/1992 | Beastall et al. |
| 5,201,779 A | | 4/1993 | Shiao |
| 5,213,566 A | | 5/1993 | Weissenburger |
| 5,330,427 A | | 7/1994 | Weissenburger |
| 5,397,312 A | | 3/1995 | Rademaker et al. |
| 5,404,870 A | | 4/1995 | Brinkerhoff et al. |
| 5,437,628 A | * | 8/1995 | Fox et al. ...................... 604/14 |
| 5,656,283 A | | 8/1997 | Brummer et al. |
| 5,662,601 A | | 9/1997 | Snead |
| 5,788,664 A | | 8/1998 | Scalise |
| 5,807,372 A | * | 9/1998 | Balzar .................... 604/385.18 |
| 5,860,946 A | | 1/1999 | Hofstatter |
| 6,027,471 A | | 2/2000 | Fallon et al. |
| D436,661 S | | 1/2001 | Berry |
| 6,168,576 B1 | | 1/2001 | Reynolds |
| 6,190,348 B1 | | 2/2001 | Tiemann et al. |
| D445,176 S | | 7/2001 | Landers |
| 6,368,300 B1 | | 4/2002 | Fallon et al. |
| 6,432,075 B1 | * | 8/2002 | Wada et al. .................... 604/15 |
| 2002/0177582 A1 | | 11/2002 | Maloney |

\* cited by examiner

APPLICATOR DEVICE FOR SUPPOSITORIES AND THE LIKE

FIELD OF THE INVENTION

The present invention relates to applicator devices for suppositories and the like and, more particularly, to an applicator device adapted for depositing suppositories and the like in a bodily cavity or passage.

BACKGROUND OF THE INVENTION

Suppository applicators have been in use for delivering suppositories to bodily cavities, such as vaginal canals and recta. Conventional applicators are equipped with barrel members for receiving suppositories and plunger members for expelling same from the barrel members. The barrel members have loading ends which are typically equipped with finger-like members or segments projecting therefrom for releasably attaching suppositories to the loading ends (see, for instance, U.S. Pat. Nos. 2,754,822; 3,667,465; 3,934,584; 4,361,150; 5,201,779; 5,404,870; and 5,860,946). The finger-like members are sized such that, when suppositories are loaded onto the loading ends, they are enclosed substantially entirely by the finger like-members.

The applicators discussed above have various disadvantages. For instance, suppositories, when exposed to moisture, tend to stick to surfaces that are in contact therewith. In such circumstances, when the applicators are exposed to relatively high humidity, suppositories loaded therein tend to stick to the loading ends of the applicators. Because the suppositories are enclosed substantially entirely by the finger-like members, they have a relatively large area of contact with the loading ends of the applicators. As a result, when the suppositories stick to the applicators during storage or use, it becomes difficult to expel same from the applicators.

SUMMARY OF THE INVENTION

The present invention overcomes the disadvantages and shortcomings discussed above by providing an improved applicator device for delivering pharmaceutical products or the like to a bodily cavity. More particularly, the device includes a barrel member having a distal end which is equipped with an opening. The applicator also includes a plurality of petals extending outwardly from the distal end in a generally axial direction. The petals cooperate with the opening so as to form a receptacle for releasably receiving a pharmaceutical product in the distal end of the barrel member. Each of the petals has a truncated flexible tip sized and shaped so as to engage a substantially central portion of the pharmaceutical product such that a large section of the pharmaceutical product extends outwardly beyond the petals so as to facilitate the release of the pharmaceutical product from the receptacle. The device also includes a plunger member for releasing the pharmaceutical product from the receptacle. In accordance with the present invention, the device can be packaged in a package together with the pharmaceutical product received in the receptacle.

BRIEF DESCRIPTION OF THE DRAWINGS

For a more complete understanding of the present invention, reference is made to the following detailed description of the present invention considered in conjunction with the accompanying drawings, in which.

DETAILED DESCRIPTION OF THE EXEMPLARY EMBODIMENTS

Figures 1, 2:
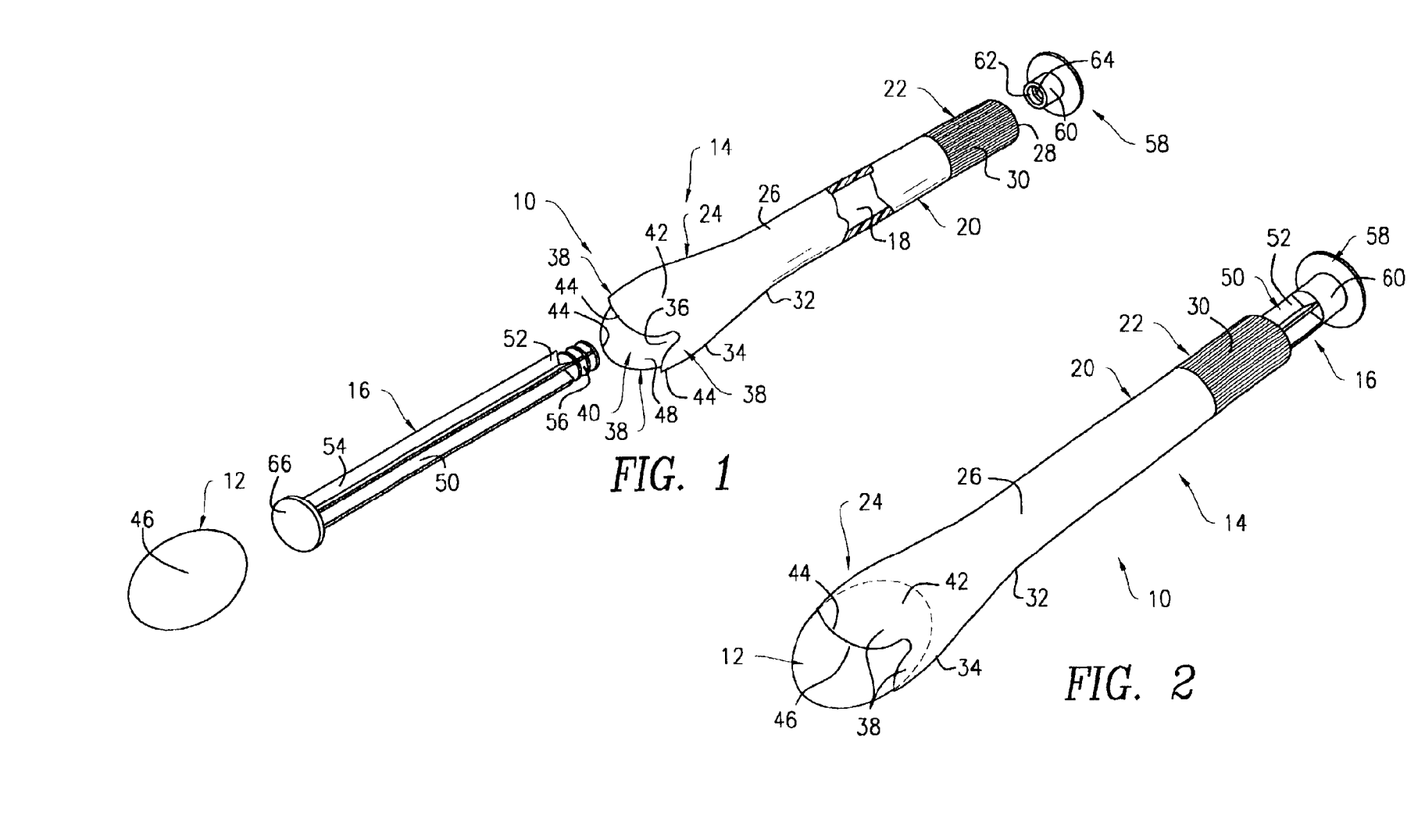
FIG. 1 is an exploded perspective view of a suppository applicator constructed in accordance with a first exemplary embodiment of the present invention.
FIG. 2 is a perspective view of the applicator of FIG. 1 in an assembled configuration ready for use.
Figure 5:
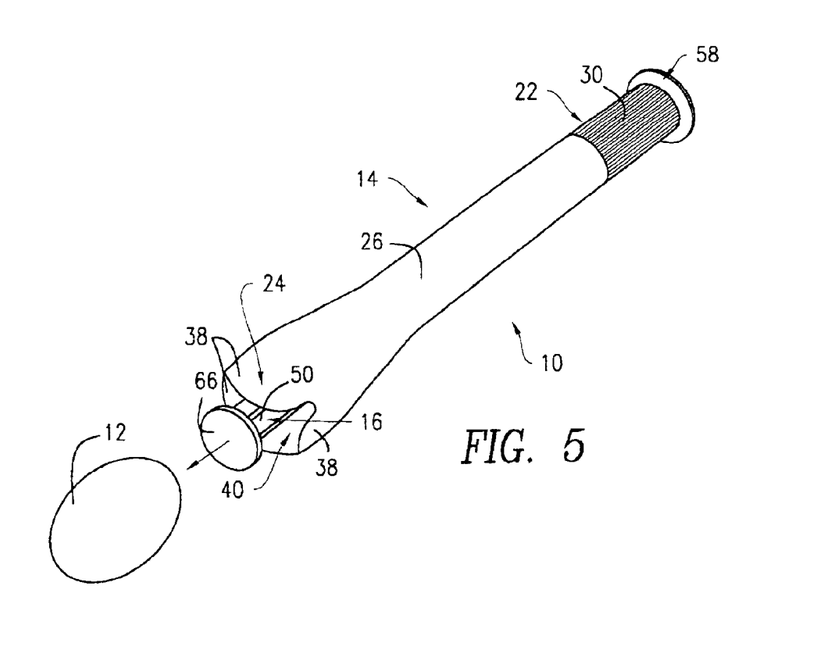
FIG. 5 is a perspective view of the applicator of FIG. 2 illustrating the dispensing of a suppository product.

Referring to FIGS. 1, 2 and 5, there is shown a suppository applicator 10 constructed in accordance with a first embodiment of the present invention. More particularly, the applicator 10 is adapted for use in depositing an oval-shaped suppository product 12 in a bodily cavity, such as a vaginal cavity, a rectum, etc. The applicator 10 includes a barrel member 14 and a plunger member 16 extending through the barrel member 14. The barrel member 14 and the plunger member 16 are made from a suitable material (e.g., thermoplastics, polyolefins, polyolefin copolymers, modified polyvinyl chloride, thermoplastic rubber compounds, polyurethanes, etc.) preferably by a conventional injection molding process. Alternatively, one or both of the barrel member 14 and the plunger member 16 can be made by using other conventional processes.

Now referring to FIGS. 1, 2 and 5–7, the barrel member 14 is provided with an interior passageway 18 extending therethrough. The barrel member 14, which has a unitary construction and an annular wall 20 defining the passageway 18, is provided with a proximal section 22, a distal section 24 and an intermediate section 26. The intermediate section 26 is located between the proximal and distal sections 22, 24. The proximal section 22 includes an open end 28, as well as a ribbed surface 30 so as to provide a gripping surface during the use of the applicator 10. The distal section 24 has a proximal end 32, which is connected to the intermediate section 26, and a distal end 34 opposite to the proximal end 32. The distal section 24 has a flaring construction (i.e., the diameter of the proximal end 32 is smaller than the diameter of the distal end 34) and has an opening 36 formed therein and communicating with the passageway 18.

Figures 6, 7:
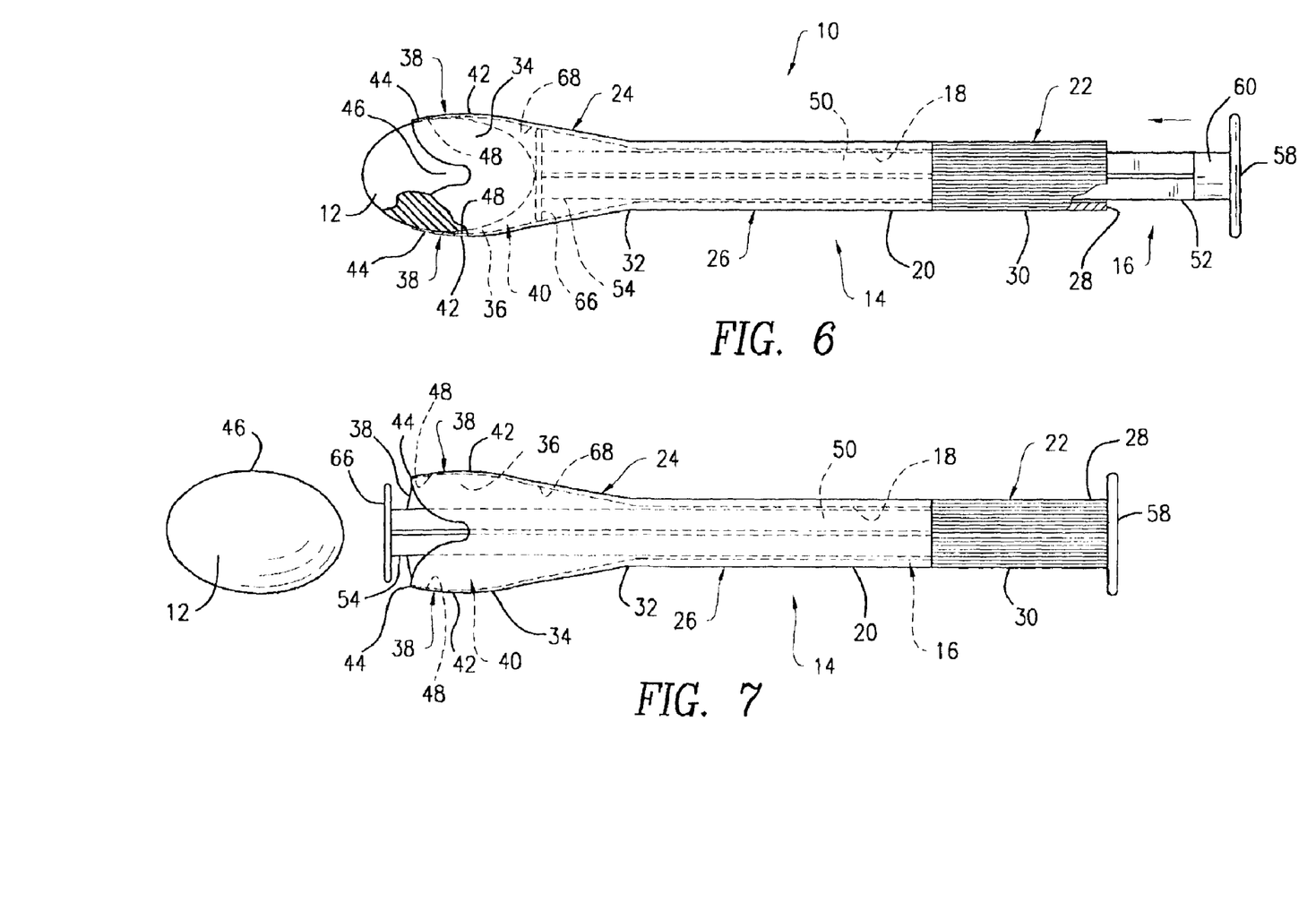
FIGS. 6 and 7 are side elevational views of the applicator shown in FIGS. 1, 2 and 5, illustrating its operation.
Figures 8, 9:
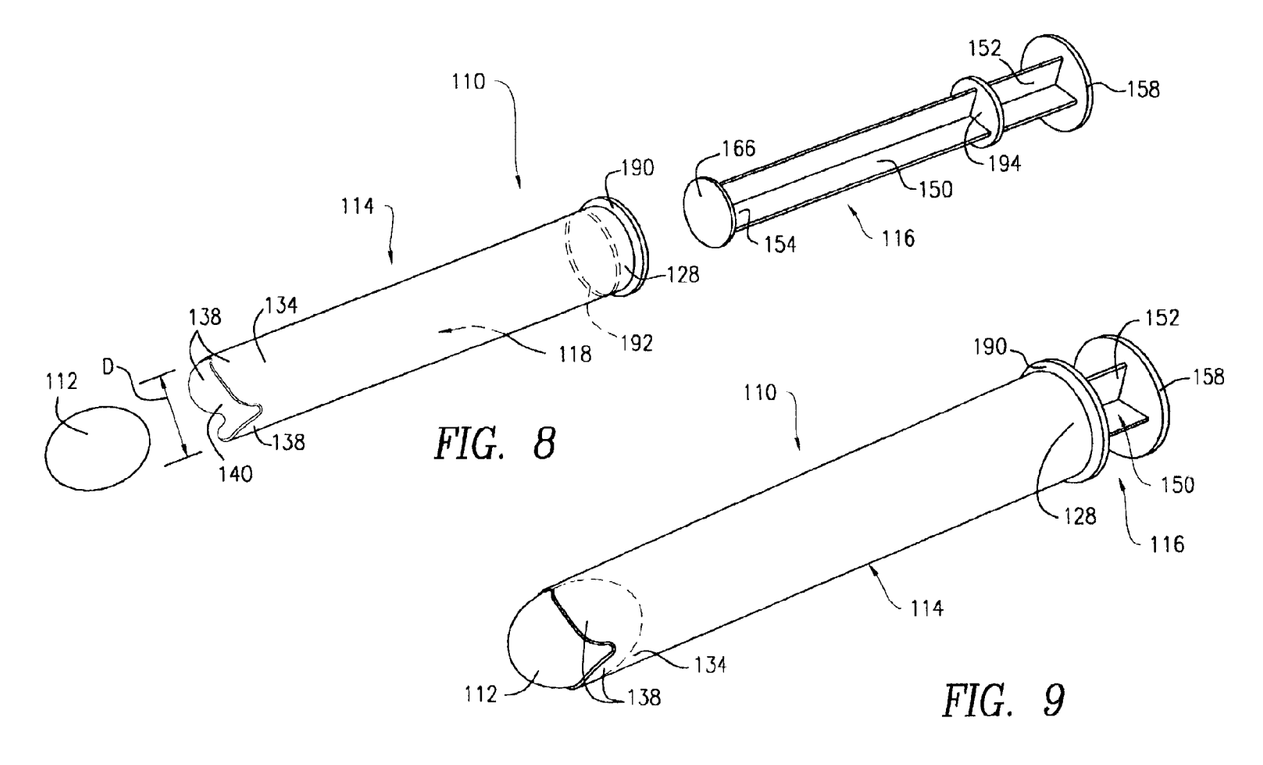
FIG. 8 is an exploded perspective view of a suppository applicator constructed in accordance with a second exemplary embodiment of the present invention.
FIG. 9 is a perspective view of the applicator of FIG. 8 in an assembled configuration ready for use.

The distal section 24 of the applicator 10 is provided with three flexible, truncated petals 38 (see FIGS. 1, 2 and 5–7) encircling the opening 36 and extending outwardly therefrom in a direction generally parallel to the longitudinal axis of the barrel member 14 (referred to hereinafter as "the axial direction") The petals 38 cooperate with the opening 36 and the distal section 24 so as to form a receptacle 40 for releasably receiving the suppository product 12 therein. Each of the petals 38 is provided with a generally semi-circular shape and has a base 42, which is integrally connected to the distal end 34 of the distal section 24, and a tip 44, which is located opposite the base 42. Due to its truncated construction, each of the petals 38 has an axial length sufficient to securely retain the suppository product 12 within the receptacle 40, but short enough to create a minimal frictional resistance to the suppository product 12 during its dispensing from the receptacle 40. With reference to FIG. 6, the petals 38 are sized and shaped such that, when the suppository product 12 is received in the receptacle 40, the tips 44 of the petals 38 engage a substantially central portion 46 of the suppository product 12 (e.g., the tips 44 are adapted to engage a portion of the suppository product 12 located slightly outwardly in the axial direction from the central portion 46 of the suppository product 12). By way of example, each of the petals 38 can have an axial length which is substantially equal to one half of the width of the suppository product 12 measured along its major axis. As a result, a substantial part of the suppository product 12 (e.g., an approximately half of the suppository product 12) extends axially beyond the receptacle 40 to facilitate easy unloading of the suppository product 12 from the receptacle 40.

Now referring to FIGS. 1, 6 and 7, each of the petals 38 is provided with a concave interior surface 48 which corresponds generally to the contour of the central portion 46 of the suppository product 12. More particularly, each of the petals 38 curves slightly inwardly in a generally radial direction as it extends from its base 42 to its tip 44 so as to engage and retain the suppository product 12 in the receptacle 40 (see FIG. 6). In this manner, even if a large part of the suppository product 12 extends beyond the tips 44 of the petals 38, the petals 38 cooperate with one another so as to retain the suppository product 12 in the receptacle 40.

Additionally, the tips 44 of the petals 38 form a second opening that maintains a larger diameter than a smallest inner diameter along the length of the barrel member 14 or the diameter at the intermediate section 26 at the interface of the proximal section 22 and distal section 24 both before and after release of the suppository product (See FIGS. 6–7).

With reference to FIG. 6, the barrel member 14 is also constructed such that the thickness of the wall 20 at the distal section 24, and more specifically at the tips 44 of the petals 38, is significantly smaller than the thickness of the wall 20 at the proximal section 22. In this manner, the petals 38 are provided with a sufficient flexibility and resiliency such that the petal tips 44 are expandable radially outwardly and contractible radially inwardly so as to permit easy loading and unloading of the suppository product 12.

Referring back to FIGS. 1, 2 and 5–7, the plunger member 16 includes a ribbed shaft 50 having a proximal end 52 and a distal end 54 and movably received in the passageway 18 of the barrel member 14. The proximal end 52 of the shaft 50 has beads 56 (see FIG. 1). A thumb platform 58 is also formed on the proximal end 52 of the shaft 50 and has a centrally positioned mounting tab 60. The mounting tab 60 has a female receptacle opening 62 (see FIG. 1) having beads 64 adapted to engage the beads 56 of the shaft 50 such that the proximal end 52 of the shaft 50 can be snap-fitted into the receptacle opening 62 of the thumb platform 58. In this manner, the thumb platform 58 is securely attached to the shaft 50 by an interference fit. A contact platform 66 is integrally formed with the distal end 54 of the shaft 50. The contact platform 66 is sized and shaped so to be received movably in the receptacle 40 of the distal section 24 of the barrel member 14 for use in discharging the suppository product 12 from the applicator 10. In this regard, the contact platform 66 has an oversized shape (i.e., has a diameter similar or substantially identical to the width of the suppository product 12 measured along its minor axis) for purposes to be discussed hereinafter.

With reference to FIGS. 2 and 5–7, the plunger member 16 is movable relative to the barrel member 14 in the axial direction between a retracted position (see FIGS. 2 and 6), in which the contact platform 66 is positioned adjacent the proximal end 32 of the distal section 24 of the barrel member 14, and an extended position (see FIGS. 5 and 7), in which the contact platform 66 is located axially outwardly from the tips 44 of the petals 38 and hence the receptacle 40. In this regard, the outer diameter of the thumb platform 58 is greater than that of the proximal section 22 of the barrel member 14 so as to prevent the plunger member 16 from moving beyond its extended position (see FIG. 7). Similarly, the outer diameter of the contact platform 66 is larger than the inner diameter of the proximal end 32 of the distal section 24 such that the contact platform 66 engages an interior portion 68 (see FIG. 6) of the distal section 24 located adjacent to the proximal end 32, thereby inhibiting the plunger member 16 from moving beyond its retracted position. When the plunger member 16 is positioned in its retracted position, the contact platform 66 abuts an end of the suppository product 12 (see FIG. 6) so as to prevent it from being positioned too far into the receptacle 40. More particularly, the contact platform 66 ensures that the suppository product 12 is cradled in the receptacle 40 in a preferred holding position, in which it is engaged by the distal section 24 of the barrel member 14 only at the tips 44 of the petals 38, thereby minimizing the area of contact between the suppository product 12 and the barrel member 14. In this regard, the receptacle 40 preferably has a size which is greater than that of the suppository product 12 such that the entire interior surface of the receptacle 40, with the exception of the tips 44 of the petals 38, is out of contact with the suppository product 12, whereby the suppository product 12 can be easily released from the receptacle 40.

Referring back to FIG. 1, the applicator 10 is assembled by inserting the shaft 50 into the passageway 18 through the opening 36 of the distal section 24 such that its proximal end 52 is extended outwardly from the open end 28 of the barrel member 14. The thumb platform 58 is then attached to the proximal end 52 of the shaft 50. The suppository product 12 is then inserted into the receptacle 40 of the applicator 10 for delivery into a bodily cavity.

Figure 3:
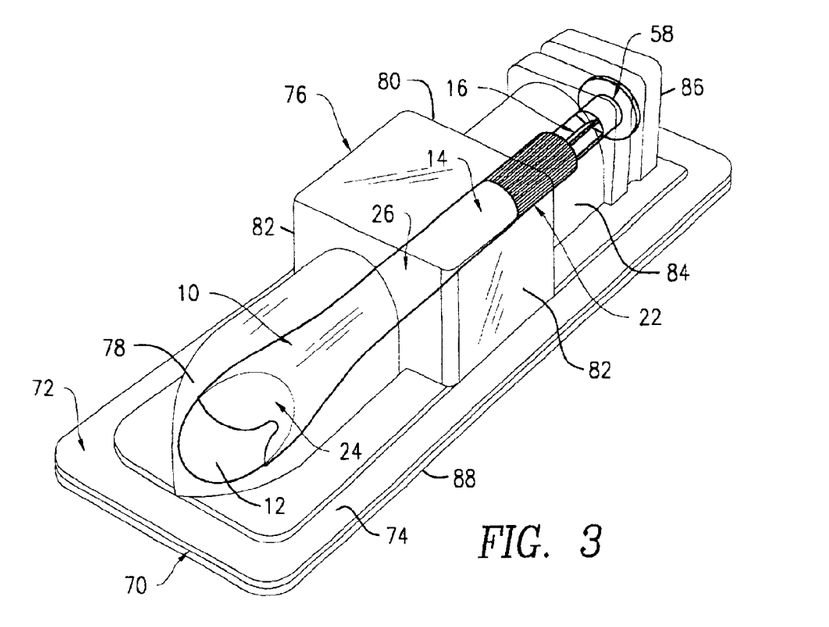
FIG. 3 is a perspective view of the applicator of FIG. 2 packaged in a blister packaging assembly.
Figure 4:
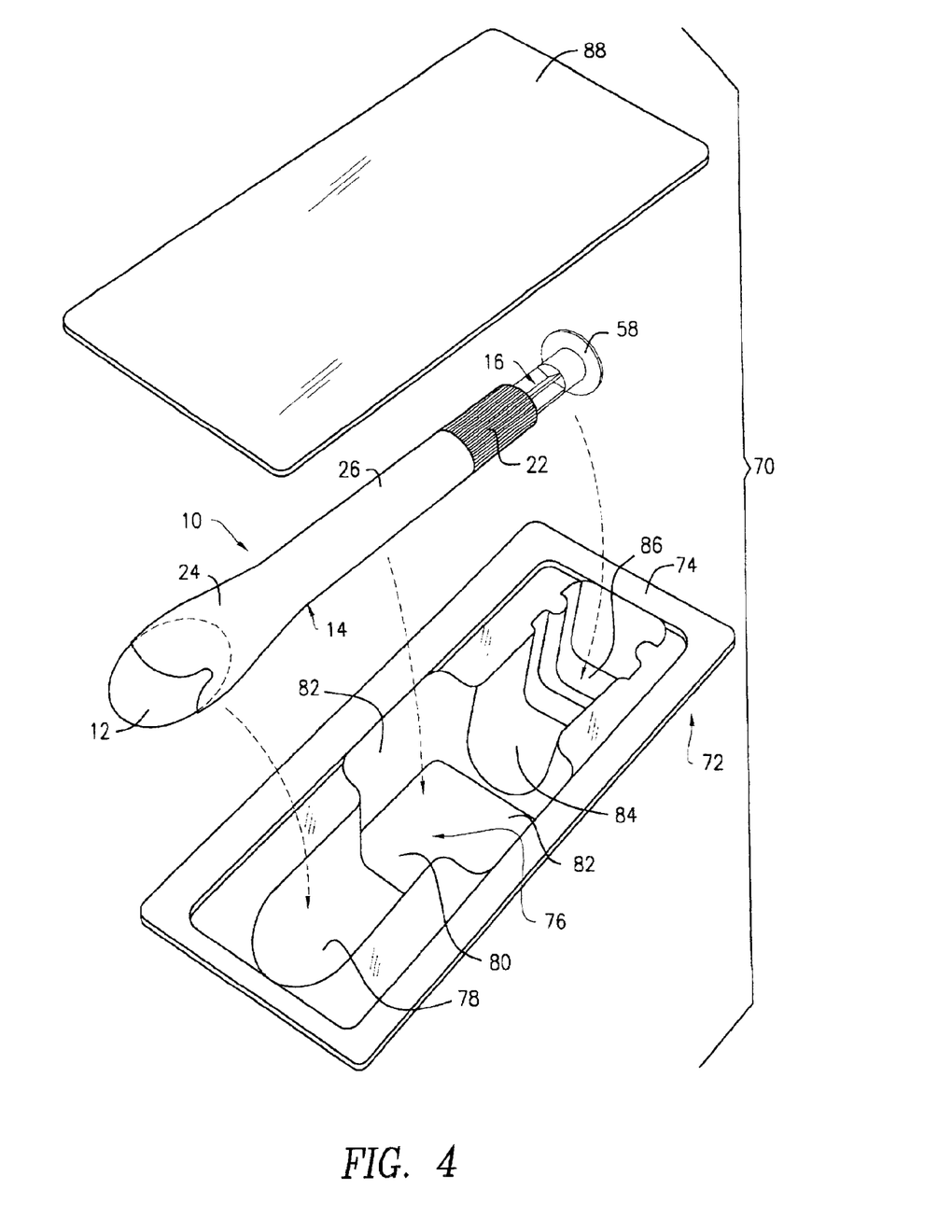
FIG. 4 is an exploded perspective view of the blister packaging assembly of FIG. 3.

The applicator 10 can be provided to a user without the suppository product 12 pre-installed in the receptacle 40. Alternatively, the applicator 10 can be provided to a user with the suppository product 12 pre-filled in the receptacle 40. When provided in its pre-filled form, the applicator 10 can be packaged in a blister packaging assembly 70 (see FIGS. 3 and 4). More particularly, the blister packaging assembly 70 includes a thermoformed, blister-type PVC (polyvinyl chloride) plastic tray 72 for receiving the pre-filled applicator 10. Alternatively, the tray 72 can be made from any other suitable materials. The tray 72 includes an outer perimeter rim 74 and a compartment 76 projecting from the rim 74. The compartment 76 includes an outer cavity section 78 for receiving the distal section 24 of the barrel member 14, including the suppository product 12 pre-installed in the receptacle 40. The compartment 76 is also equipped with an intermediate cavity section 80 for receiving the intermediate section 26 of the barrel member 14. The intermediate cavity section 80 includes a pair of side extensions 82 for receiving user's fingers during the removal of the applicator 10 from the tray 72. An intermediate cavity section 84 is also connected to the intermediate cavity section 80 for receiving the proximal section 22 of the barrel member 14, while an outer cavity section 86 is connected to the intermediate cavity section 84 for receiving the thumb platform 58 of the plunger member 16. A peelable lid 88 laminated with an aluminum foil is attached to the packaging tray 72 in a conventional manner for sealing the applicator 10 in the compartment 76.

In order to use the pre-filled applicator 10 packaged in the packaging assembly 70, the applicator 10 is removed from the packaging assembly 70. The distal section 24 of the applicator 10, together with the suppository product 12 attached thereto, is then inserted into a vaginal canal (not shown) in a conventional manner. In doing so, the barrel member 14 is gripped by the user's fingers at the ribbed surface 30 of the proximal section 22. After properly placing the distal section 24 and the suppository product 12 in the vaginal canal, the thumb platform 58 of the plunger member 16 is pushed toward the distal section 24 of the barrel member 14 so as to move the barrel member 14 from its retracted position (see FIGS. 2 and 6) to its extended position (see FIGS. 5 and 7). In this regard, the applicator 10 can be held and operated by the user in any conventional manner. For instance, with the proximal section 22 of the barrel member 14 held by the user's index and middle fingers, the thumb platform 58 of the plunger member 16 can be pushed by the user's thumb. As the plunger member 16 moves from its retracted position to its extended position (as indicated by the arrow in FIG. 6), the contact platform 66 of the plunger member 16 pushes the suppository product 12 out of the receptacle 40. During the release of the suppository product 12 from the receptacle 40, the tips 44 of the petals 38 expand in a radially outward direction so as to facilitate the release of the suppository product 12. In order to ensure the release of the suppository product 12 from the applicator 10, the thumb platform 58 is pushed until the plunger member 16 is positioned in its extended position, in which the contact platform 66 is located axially outwardly from the receptacle 40 (see FIGS. 5 and 7).

After the release of the suppository product 12 from the applicator 10 into the vaginal canal, the plunger member 16 is pulled back into its retracted position so as to place the contact platform 66 within the receptacle 40. In this manner, during the removal of the applicator 10 from the vaginal cavity, the contact platform 66 is prevented from coming in contact with tissue walls of the vaginal cavity and causing injury to same. The applicator 10 is then cleaned and disinfected for subsequent use or is discarded.

It should be appreciated that the applicator 10 of the present invention provides numerous advantages over conventional applicators. For instance, because the petals 38 of the applicator 10 have a truncated construction, they are adapted to retain the suppository product 12 in the receptacle 40, while permitting easy release of same from the receptacle 40. As a result, the suppository product 12 can be released from the applicator 10 in response to the application of an axial force that is significantly less than the force required for conventional applicators. In this manner, even if the suppository product 12 sticks to the interior surface of the receptacle 40 during its storage or insertion into a bodily cavity, it can be released from the receptacle 40 without significant difficulty. Because of its ability to release the suppository product 12 stuck to the receptacle 40, the applicator 10 can be provided to users in pre-filled and packaged form.

The oversized contact platform 66 of the plunger member 16 further ensures the proper dispensing of the suppository product 12 from the receptacle 40. For instance, because of its large size, the contact platform 66 tends to apply an axial force evenly to the suppository product 12, thereby minimizing distortion of the suppository product 12 during its release from the receptacle 40. Moreover, the contact platform 66 functions to strip the suppository product 12 off the interior surface of the receptacle 40 if there is excess friction or sticking between the suppository product 12 and the barrel member 14. In addition, because the suppository product 12 is mounted to the flaring distal section 24, the remaining sections of the barrel member 14 (i.e., the intermediate and proximal sections 26, 22) can be made relatively slender.

It should be noted that the applicator 10 of the present invention can have numerous modifications and variations. For instance, the applicator 10 can be provided with a different number of petals 38. Moreover, although the present invention is especially suitable for use in delivering suppository products to vaginal canals or cavities, it can be used to dispense suppository products or other pharmacological products in other body cavities such as a rectum. Further, the applicator 10 can be modified to accommodate suppository products having different geometrical shapes. In addition, the petals 38 can be provided with different shapes and lengths. The applicator 10 can also be packaged in different types of packages.

A second exemplary embodiment of the present invention is illustrated in FIGS. 8–13. Elements illustrated in FIGS. 8–13 which correspond to the elements described above with reference to FIGS. 1–7 have been designated by corresponding reference numbers increased by one hundred. Unless stated otherwise, the second exemplary embodiment of FIGS. 8–13 is constructed, used and operated in the same basic manner as the exemplary embodiment shown in FIGS. 1–7.

With reference to FIGS. 8, 9, 12 and 13, there is shown a suppository applicator 110 constructed in accordance with the second embodiment of the present invention. The applicator 110, which is adapted for use in delivering an oval-shaped suppository product 112 to a bodily cavity (e.g., a vaginal orifice), includes a barrel member 114 having an open proximal end 128 and an open distal end 134. Unlike the barrel member 14 of the embodiment of FIGS. 1–7, the entire barrel member 114 is substantially cylindrical in shape and is slightly tapered as it extends from the proximal end 128 to the distal end 134 (i.e., the diameter of the proximal end 128 is slightly greater than that of the distal end 134). As a result, the distal end 134 of the barrel member 114 is not flared. The barrel member 114 includes an interior passageway 118 extending between the proximal and distal ends 128, 134. A perimeter rim wall 190 is formed at the proximal end 128, while an annular retaining rib 192 is formed in the passageway 118 adjacent the proximal end 128. Flexible, truncated petals 138 are also formed at the distal end 134 of the barrel member 114. The petals 138 cooperate with one another so as to define a receptacle 140 for receiving the suppository product 112.

Still referring to FIGS. 8, 9, 12 and 13, the applicator 110 also includes a plunger member 116 having a single-piece construction. More particularly, the plunger member 116 includes a ribbed shaft 150, a proximal end 152 and a distal end 154. A thumb platform 158 is formed at the proximal end 152 for engagement with the rim wall 190 of the barrel member 114, while a contact platform 166 is formed at the distal end 154. The contact platform 166 has a diameter smaller than the inner diameter of the retaining rib 192 of the barrel member 114 such that it can be inserted into the passageway 118. The diameter of the contact platform 166 is also larger than an inner diameter D (see FIG. 8) of the receptacle 140 defined by the petals 138 such that, when the contact platform 166 is positioned in the receptacle 140, it comes in contact with the petals 138 and causes same to flex radially outwardly (see FIG. 13), thereby facilitating the release of the suppository product 112 from the receptacle 140. A stopping platform 194 is formed on the shaft 150 adjacent to the proximal end 152 of the shaft 150. The stopping platform 194 has a diameter slightly larger than the inner diameter of the retaining rib 192 of the barrel member 114 for purposes to be discussed hereinafter. In this regard, the stopping platform 194 is slightly flexible such that it can be inserted into the passageway 118 from the proximal end 128 of the barrel member 114 and positioned between the retaining rib 192 and the distal end 134.

The plunger member 116 is movably mounted in the passageway 118 of the barrel member 114. As a result, the plunger member 116 is movable relative to the barrel member 114 between a retracted position (see FIG. 12), in which the contact platform 166 is located remote from the petals 138, and an extended position, in which the contact platform 166 is in contact with the petals 138 (see FIG. 13). In this regard, the retaining rib 192 of the barrel member 114 is engageable with the stopping platform 194 of the plunger member 116 so as to inhibit the plunger member 116 from moving beyond its retracted position. Similarly, the rim wall 190 of the barrel member 114 is adapted to engage the thumb platform 158 of the plunger member 116 for the purpose of inhibiting it from moving beyond its extended position.

Figure 10:
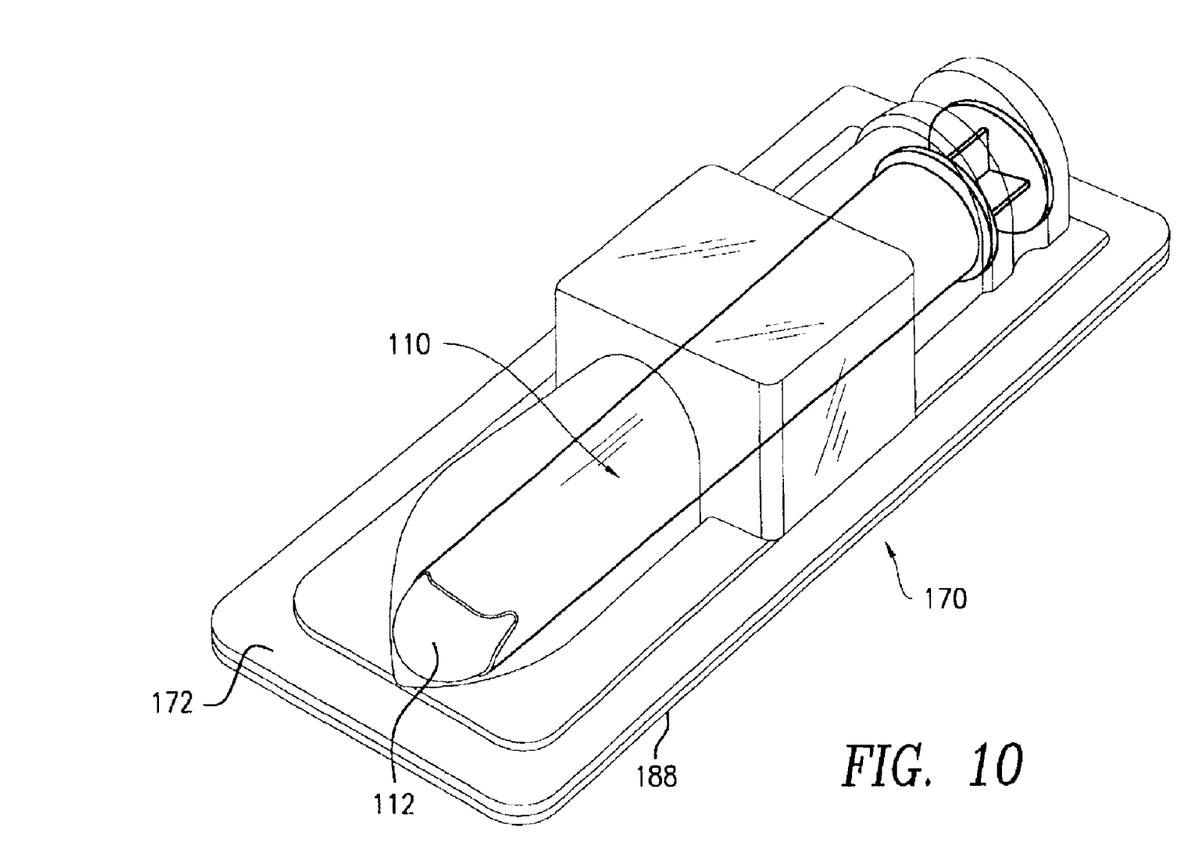
FIG. 10 is a perspective view of the applicator of FIG. 9 packaged in a blister packaging assembly.
Figure 11:
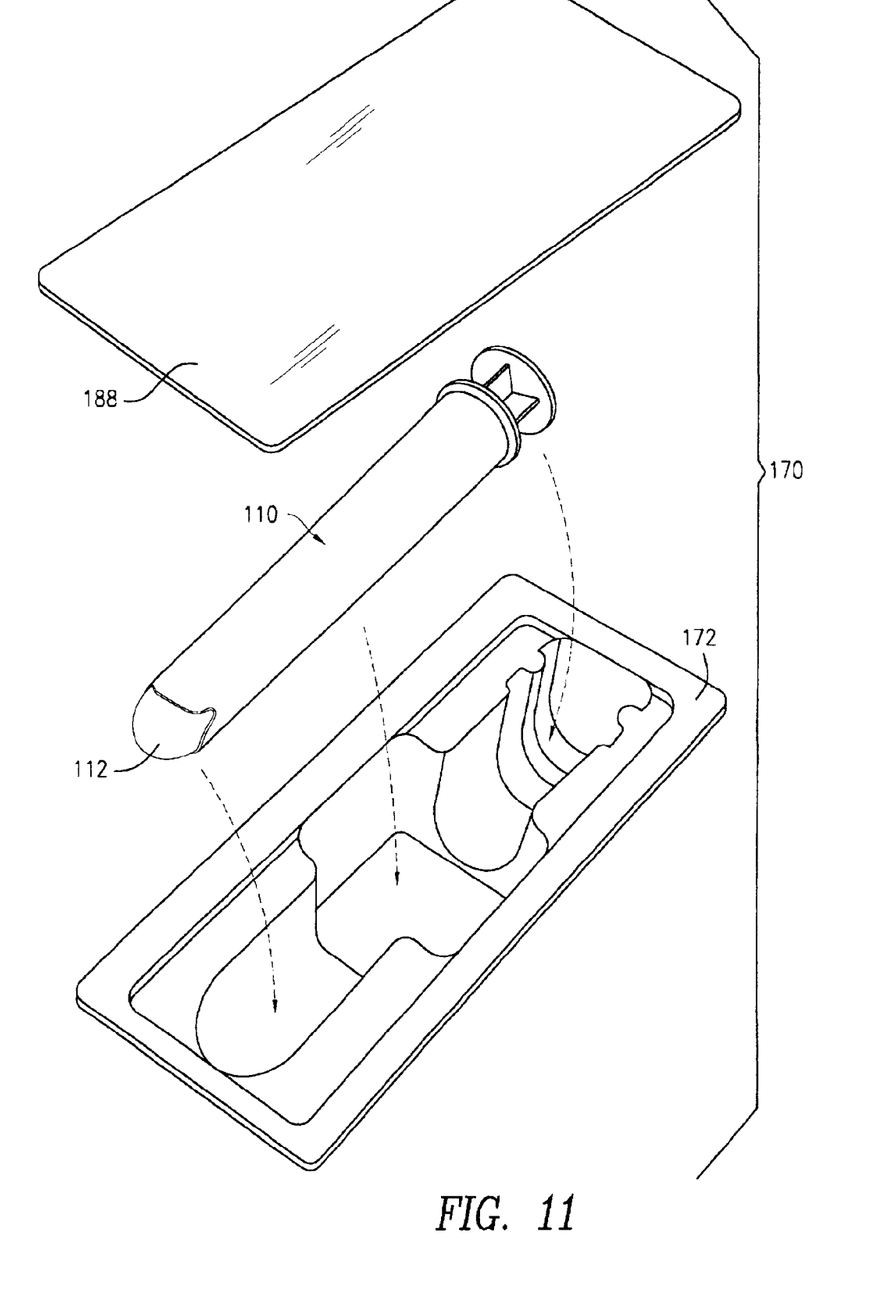
FIG. 11 is an exploded perspective view of the blister packaging assembly of FIG. 10.
Figure 12:
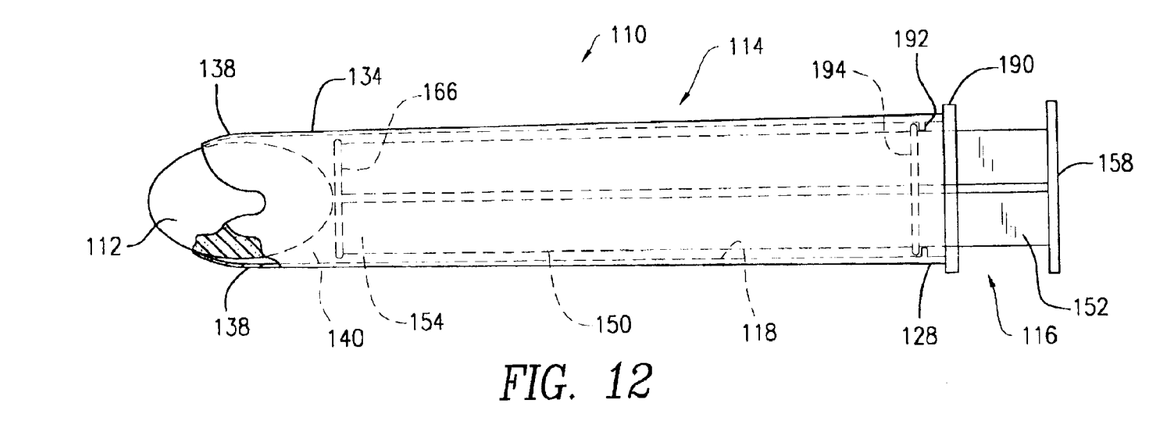
FIGS. 12 and 13 are side elevational views of the applicator shown in FIGS. 8 and 9, illustrating its operation.
Figure 13:
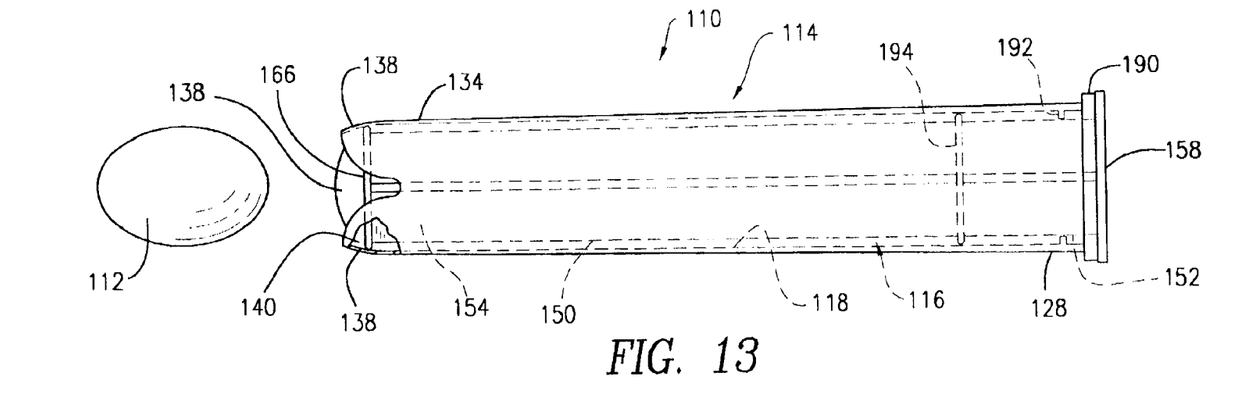

With reference to FIGS. 10 and 11, a blister packaging assembly 170 is provided for packaging the applicator 110 pre-filled with the suppository product 112. More particularly, the packaging assembly 170 has a construction basically identical to that of the blister packaging assembly 70 of the embodiment shown in FIGS. 1–7. For instance, the packaging assembly 170 has a tray 172 for receiving the pre-filled applicator 110 and a peelable lid 188 attached to the tray 172.

It will be understood that the embodiments described herein are merely exemplary and that a person skilled in the art may make many variations and modifications without departing from the spirit and scope of the invention. All such variations and modifications, including those discussed above, are intended to be included within the scope of the invention.

I claim:

1. An assembly comprising a pharmaceutical product; and a device for delivering said pharmaceutical product to a bodily cavity, said device including a barrel member having a distal end, which includes an opening, and a plurality of petals extending outwardly from said distal end in a generally axial direction, said petals cooperating with said opening so as to form a receptacle in said distal end of said barrel member for releasably receiving said pharmaceutical product each of said petals including a base connected to said distal end of said barrel member and terminating at a truncated flexible tip, each of said petals including an intermediate section extending between a corresponding one of said bases and a corresponding one of said tips, each of said petals being sized and shaped such that the entire portion of each of said intermediate sections is spaced from said pharmaceutical product in a radially outward direction and such that only said tips engage said pharmaceutical product at a substantially central portion thereof when said pharmaceutical product is fully received in said receptacle; and wherein the tips of the petals form a second opening that maintains a larger diameter than a smallest inner diameter along the length of the barrel member both before and after release of the pharmaceutical product.

2. The assembly of claim 1, wherein said opening is encircled by said petals.

3. The assembly of claim 1, wherein each of said petals is flexible such that said tips are expandable and contractible in said radial direction.

4. The assembly of claim 3, wherein said petals are sized and shaped such that approximately half of said pharmaceutical product received in said receptacle extends outwardly beyond said tips.

5. The assembly of claim 4, wherein the curvature of each of said tips corresponds generally to the curvature of a substantially central portion of said pharmaceutical product received in said receptacle.

6. The assembly of claim 5, wherein said petals are sized and shaped so as to receive an oval-shaped suppository product.

7. The assembly of claim 1, wherein each of said petals has a length measured in said axial direction, said length being about one-half of an axial length of said pharmaceutical product received in said receptacle.

8. The assembly of claim 7, wherein each of said petals has a substantially semi-circular shape.

9. The assembly of claim 1, wherein said barrel member includes a proximal end, which is located opposite to said distal end, a substantially annular wall and a passageway extending between said distal and proximal ends through said wall.

10. The assembly of claim 9, wherein said wall has a first thickness at said tips and a second thickness at said proximal end, said first thickness being substantially less than said second thickness.

11. The assembly of claim 10, wherein said barrel member has a proximal section adjacent said proximal end and a distal section adjacent said distal end, said distal section having a flared shape.

12. The assembly of claim 11, wherein said distal end has a first radius and said proximal end has a second radius, said first radius being greater than said second radius.

13. The assembly of claim 12, wherein said barrel member includes an intermediate section positioned between said proximal and distal ends, said distal section including a proximal end portion integrally connected to said intermediate section of said barrel member and a distal end portion defined by said distal end of said barrel member, said distal and proximal end portions having third and fourth radii, respectively, said third radius being greater than said fourth radius.

14. The assembly of claim 1, further comprising a plunger member movably extending through a passageway of said barrel member for releasing said pharmaceutical product received in said receptacle.

15. The assembly of claim 14, wherein said plunger member has a distal end and a contact platform attached to said distal end of said plunger member for applying an axial force to said pharmaceutical product received in said receptacle.

16. The assembly of claim 15, wherein said contact platform has a size similar to the size of said pharmaceutical product received in said receptacle so as to substantially evenly distribute an axial force to said pharmaceutical product.

17. The assembly of claim 14, wherein said plunger member is axially movable relative to said barrel member between a first position, in which said contact platform is retracted into said receptacle so as to permit the loading of said pharmaceutical product in said receptacle, and a second position, in which said contact platform is positioned adjacent said tips so as to expel said pharmaceutical product from said receptacle.

18. The assembly of claim 17, wherein when said plunger member is positioned in its said first position, said contact platform is positioned in said receptacle and is in contact with said pharmaceutical product received in said receptacle so as to properly orient said pharmaceutical product such that said distal end of said barrel member is in contact with said pharmaceutical product only at said tips.

19. The assembly of claim 18, wherein said contact platform is positioned outwardly beyond said petals when said plunger member is positioned in its said second position.

20. The assembly of claim 18, further comprising first restricting means for restricting said plunger member from moving beyond its said first position.

21. The assembly of claim 20, further comprising second restricting means for restricting said plunger member from moving beyond its said second position.

22. The assembly of claim 21, wherein said barrel member includes a distal section located adjacent said distal end of said barrel member and having a flared shape, said first restricting means including a portion formed as part of said distal section and sized and shaped so as to engage said contact platform.

23. The assembly of claim 21, wherein said second restricting means includes a flange formed on a proximal end of said plunger member and sized and shaped so as to engage a proximal end of said barrel member.

24. The assembly of claim 1, wherein each adjacent pair of said petals is separated by a slit having a generally triangular shape.

25. The assembly of claim 24, wherein each of said slits has a first end positioned adjacent said barrel member and a second end positioned remote from said barrel member, said first and second ends having first and second widths, respectively, said second width being substantially greater than said first width.

26. The assembly of claim 1, wherein said barrel member has a proximal end, which is located opposite said distal end, a first section, which has an end remote from said proximal end of said barrel member, and a second section, which extends from said end of said first section in said axial direction and terminates at said distal end of said barrel member, said barrel member having a first diameter at the interface between said first and second sections and a second diameter at said distal end of said barrel member, said second section has a flared shape such that said second diameter is greater than said first diameter, said petals curving inwardly in a generally radial direction as they extend in said axial direction from said distal end of said barrel member to said tips.

27. An assembly comprising a pharmaceutical product and a assembly for delivering said pharmaceutical product to a bodily cavity, said device including a barrel member having a distal end, which includes an opening, and a plurality of petals extending outwardly from said distal end in a generally axial direction, said petals cooperating with said opening so as to form a receptacle, said pharmaceutical product being releasably received in in siad recebtack said distal end of said barrel member, each of said petals including a base connected to said distal end of said barrel member and terminating at a truncated flexible tip, each of said petals including an intermediate section extending between a corresponding one of said bases and a corresponding one of said tips, each of said petals being sized and shaped such that the entire portion of each of said intermediate sections is spaced from said pharmaceutical product in a radially outward direction and such that only said tips engage said pharmaceutical product at a substantially central portion thereof when said pharmaceutical product is fully received in said receptacle, whereby a large section of said pharmaceutical product extends outwardly beyond said petals so as to facilitate the release of said pharmaceutical product from said receptacle; and packaging means for packaging said assembly together with said pharmaceutical product; and wherein the tips of the petals form a second opening that maintains a larger diameter than a smallest inner diameter along the length of the barrel member both before and after release of the pharmaceutical product.

28. The assembly of claim 27, wherein said packaging means includes a tray for receiving said device and said pharmaceutical product and a lid removably attached to said tray.

29. The assembly of claim 28, wherein said tray is a blister-type tray.

30. A device for delivering pharmaceutical products or the like to a bodily cavity, comprising a barrel member having a distal end, which includes an opening, a proximal end, which is located opposite said distal end, a first section, which extends from said proximal end and which has an end remote from said proximal end of said barrel member, and a second section, which extends from said end of said first section in a generally axial direction and terminates at said distal end of said barrel member, said barrel member having a first diameter at an interface between said first and second sections and a second diameter at said distal end of said barrel member, said second section having a flared shape such that said second diameter is greater than said first diameter, said barrel member having a plurality of petals extending outwardly from said distal end in said axial direction, said petals cooperating with said opening so as to form a receptacle in said distal end of said barrel member releasably receiving a pharmaceutical product each of said petals having a truncated flexible tip, said petals curving inwardly in a generally radial direction as they extend in said axial direction from said distal end of said barrel member to said tips, and said tips sized and shaped so as to engage a substantially central portion of the pharmaceutical product such that when the pharmaceutical product is fully received in said receptacle, a large section of the pharmaceutical product extends outwardly beyond said petals so as to facilitate the release of a pharmaceutical product received in said receptacle; and wherein the tips of the petals form a second opening that maintains a larger diameter than the first diameter at the interface between the first and second sections both before and after release of the pharmaceutical product.

31. The device of claim 30, wherein said petals engage a pharmaceutical product only at said tips when the pharmaceutical product is fully inserted into said receptacle.

32. The device of claim 31, wherein said petals are sized and shaped such that approximately half of a pharmaceutical product received in said receptacle extends outwardly beyond said tips.

* * * * *